United States Patent
Snyder et al.

(10) Patent No.: US 6,491,623 B2
(45) Date of Patent: Dec. 10, 2002

(54) DEVICE FOR PREVENTING FECAL INCONTINENCE

(75) Inventors: Daniel R. Snyder, Branford, CT (US); Harriet A. Fellows, Haddam, CT (US)

(73) Assignee: Harridan Medical, Branford, CT (US)

( * ) Notice: Subject to any disclaimer, the term of this patent is extended or adjusted under 35 U.S.C. 154(b) by 14 days.

(21) Appl. No.: 09/769,504

(22) Filed: Jan. 25, 2001

(65) Prior Publication Data

US 2001/0041823 A1 Nov. 15, 2001

Related U.S. Application Data

(60) Provisional application No. 60/178,349, filed on Jan. 25, 2000.

(51) Int. Cl.$^7$ .................................................. A61F 2/04
(52) U.S. Cl. ........................................................ 600/31
(58) Field of Search ............................... 600/29–32, 37; 604/27–28; 606/139, 140, 151, 201–203, 213, 228; 607/41; 128/897–899, DIG. 25

(56) References Cited

U.S. PATENT DOCUMENTS

| | | | | |
|---|---|---|---|---|
| 3,863,662 A | * | 2/1975 | Zehr ........................... 137/377 |
| 4,417,567 A | * | 11/1983 | Trick ................... 128/DIG. 25 |
| 4,584,990 A | * | 4/1986 | Haber et al. ......... 128/DIG. 25 |
| 4,634,443 A | * | 1/1987 | Haber ................. 128/DIG. 25 |
| 4,643,169 A | * | 2/1987 | Koss et al. .......... 128/DIG. 25 |
| 4,682,583 A | * | 7/1987 | Burton et al. ........ 128/DIG. 25 |
| 4,878,889 A | * | 11/1989 | Polyak ................ 128/DIG. 25 |
| 4,881,939 A | * | 11/1989 | Newman ............. 128/DIG. 25 |
| 4,994,019 A | * | 2/1991 | Fernandez et al. ... 128/DIG. 25 |
| 5,509,888 A | * | 4/1996 | Miller ................. 128/DIG. 25 |
| 5,562,598 A | * | 10/1996 | Whalen et al. ...... 128/DIG. 25 |
| 6,045,498 A | * | 4/2000 | Burton et al. ............... 128/898 |
| 6,074,341 A | * | 6/2000 | Anderson et al. .... 128/DIG. 25 |

* cited by examiner

Primary Examiner—Kevin Shaver
Assistant Examiner—Joseph A. Cadugan
(74) Attorney, Agent, or Firm—Cummings & Lockwood

(57) ABSTRACT

An implantable device for controlling a body conduit including a cuff portion adapted to substantially encircle a body conduit. An inlet tube is operatively connected for delivering fluid to the cuff portion. The inlet tube has a one-way valve. An outlet tube is operatively connected to the cuff portion for releasing fluid therefrom and includes a normally closed valve. A pumping reservoir is in communication with the inlet tube and the outlet tube, wherein manipulation of the pumping reservoir inflates the cuff portion and manipulation of the normally closed valve deflates the cuff portion. An inflatable lumen surrounds the pumping reservoir and the cuff portion to provide rigidity and balance pressure between the cuff portion and the pumping reservoir.

20 Claims, 11 Drawing Sheets

DEVICE FOR PREVENTING FECAL INCONTINENCE

CROSS-REFERENCE TO RELATED APPLICATION

This application claims priority to U.S. Provisional Patent Application No. 60/178,349 filed Jan. 25, 2000, which is incorporated herein by reference.

BACKGROUND OF THE INVENTION

1. Field of the Invention

The subject disclosure relates to systems for artificially constricting body conduits, and more particularly to an improved artificial sphincter for preventing fecal incontinence.

2. Background of the Related Art

In the medical field, colostomies, Krohn's disease, short-gut syndrome in children, bowel resections for colorectal carcinoma and a variety of other circumstances can cause an individual to become incontinent. To accommodate such conditions, it is desirable to artificially constrict a body conduit or otherwise stop the flow of biological material therethrough.

Several devices have been developed to perform this function. For example, U.S. Pat. No. 3,750,194 to Summers discloses an apparatus for reversibly closing a body passage which includes a pump activated by an external switch to fill or empty a band, which acts as an artificial internal sphincter. U.S. Pat. No. 4,428,365 to Hakky discloses an anti-incontinent prosthesis which includes a strip of silicone rubber which has three bladders which are connected to tubing. The tubing connects the bladders to a flexible bulb. A non-return valve, between the bulb and the tubing, can be deformed to open the valve allowing the bladders to deflate. Pinching the flexible bulb fills the bladders with fluid.

Further examples include U.S. Pat. No. 4,634,443 to Haber, which discloses an elastofluidic sphincter having an occlusion cuff surrounding an expandable chamber. Primary and secondary fluid paths communicate with inlets and outlets of the expansible chamber. The fluid paths consist of several tube connectors and manually manipulatable one way check valves communicating with patient controlled hemispheric fluid reservoir-actuators. Depression of the fluid reservoirs increases pressure in the expansible chamber and manual manipulation of the check valves relieves pressure within the expansible chamber. A physician control port connected to the primary path facilitates adding more fluid to the system at any time.

Still further, U.S. Pat. No. 4,222,377 to Burton discloses a pressure regulated artificial sphincter having cuff member which encircles an affected vessel. A variable volume chamber, communicating with the cuff member, regulates system pressure. The cuff member receives fluid from hoses attached to a pump. Squeezing the pump introduces fluid into the cuff and chamber. A check valve prevents backflow when the pump is not being squeezed. To release the pressure within the cuff member, a tip portion of stem is depressed to overcome a spring tension against a blocking plug to unblock the check valve. U.S. Pat. No. 4,351,322 to Prager discloses a stoma control device having a ring for surgical implantation around an emerging bowel. The ring can be a gel filled skin containing a balloon which inflates to block the stoma.

Also, U.S. Pat. No. 4,994,020 to Polyak discloses an artificial sphincter which includes a cuff having a non-elastic backing and an inflatable inner cushion. The cuff is in fluid communication with a pump bulb by means of a tube. The tube has a one way check valve and a deactivation valve. U.S. Pat. No. 5,893,826 to Salama discloses an artificial sphincter. The artificial sphincter includes an inflatable balloon cuff which receives fluid through a tube from a syringe-type bulb pump connected to a one-way valve. The patient squeezing the valve with their fingers opens the valve and allows the cuff to deflate. The bulb pump is constructed of rubber or plastic with sufficient memory to allow it to maintain shape.

In light of the foregoing, a need exists for an artificial sphincter which is simple, reliable, cost-effective and which will not fail or damage the adjoining tissue.

SUMMARY OF THE INVENTION

The present disclosure provides an device for controlling the flow of matter through a body including a cuff portion configured to substantially encircle a section of a body conduit. An inlet conduit is operatively connected to the cuff portion for delivering fluid. The inlet conduit has a first flow control device operatively associated therewith. An outlet conduit is operatively connected to the cuff portion for releasing fluid therefrom. The outlet conduit has a second flow control device. A pumping reservoir is in fluid communication with the inlet conduit and the outlet conduit, wherein actuation of the pumping reservoir causes fluid to ingress into the cuff portion such that the cuff portion radially contracts and actuation of the second flow control device causes fluid to egress from the cuff portion such that the cuff portion radially expands. A lumen surrounds the cuff portion for admitting a fluid to provide rigidity and balance the pressure between the cuff portion and the pumping reservoir.

Another embodiment of the present disclosure is an artificial sphincter having an inflatable cuff for occluding a body passageway. The inflatable cuff has an interior wall portion and an exterior wall portion, wherein a first lumen is defined between the exterior wall portion and the interior wall portion, and a second lumen is defined by the interior wall portion. A pumping reservoir is in fluid communication with the inflatable cuff for controlling the ingress and egress of fluid to and from the second lumen to cause the inflatable cuff to radially contract and expand relative to the body passageway.

Still another embodiment of the present disclosure includes an implantable device for reversibly closing a body passageway. The device includes a coil having an elastic radially inner portion configured to be positioned about a body passageway such that when pressure within the coil increases, the elastic radially inner portion expands radially inward to block the body passageway. When pressure decreases, the elastic radially inner portion contracts and the body passageway opens. An outer housing provides structural support to the coil and a port is provided to inject fluid into the outer housing to adjust the rigidity of the outer housing. A reservoir stores fluid to reversibly inflate the coil by way of the at least one tube operatively connecting the coil to the reservoir. The tube has a valve to prevent backflow of fluid from the at least one coil into the reservoir and allow opening to allow fluid to flow from the coil into the reservoir.

Yet another embodiment of the present disclosure includes an artificial sphincter for controlling incontinence which has a cuff in the form of at least part of a turn of a coil. The cuff has an outer wall, an intermediate wall and an elastic inner wall. The outer wall and intermediate wall define a first lumen therebetween and the intermediate wall and the elastic inner wall define a second lumen therebetween. An injection port is provided to allow a surgeon to inflate the first lumen to set shape and rigidity but not to occlude the bowel and a pumping reservoir allows the patient to reversibly inflate and deflate the second lumen.

These and other unique features of the system disclosed herein will become more readily apparent from the following description, the accompanying drawings and the appended claims.

BRIEF DESCRIPTION OF THE DRAWINGS

So that those having ordinary skill in the art to which the disclosed system appertains will more readily understand how to make and use the same, reference may be had to the drawings wherein.

DETAILED DESCRIPTION OF THE PREFERRED EMBODIMENTS

The subject disclosure relates to an improved device for occluding a body conduit. The device is particularly applicable to serving as an artificial sphincter, although the device may be utilized in many applications, such as to treat urinary dysfunction, as would be readily appreciated by those skilled in the art.

The advantages and other features of the device disclosed herein will become more readily apparent to those having ordinary skill in the art from the following detailed description of certain preferred embodiments of the invention taken in conjunction with the drawings which set forth representative embodiments of the present disclosure and wherein like reference numeral identify similar structures.

Figure 1:
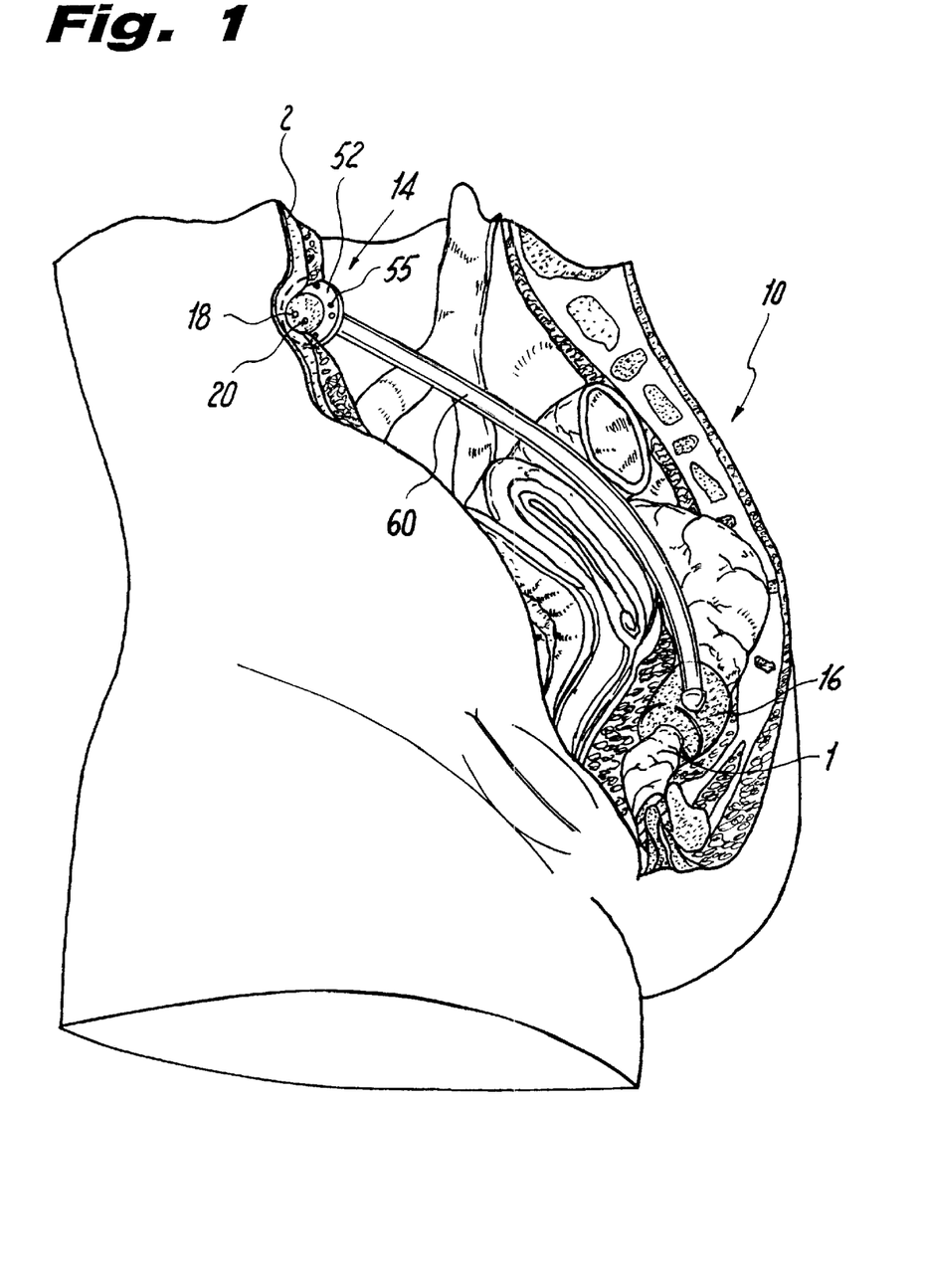
FIG. 1 illustrates a device for preventing fecal incontinence constructed in accordance with subject disclosure, and in particular a sectional view of the abdominal region of a patient having the artificial sphincter fully disposed in an operational position.

Referring to FIG. 1, an artificial sphincter, designated generally by reference numeral 10, includes a cuff portion 16 configured to occlude a body passageway. It is envisioned that the body passageway is the large bowel or descending colon 1. A pumping reservoir 14 extends from and is in fluid communication with the cuff portion 16. A first injection port 18 and a second injection port 20 in pumping reservoir 14 are adapted to allow a surgeon to inject hydraulic fluid with a syringe device 57 into the artificial sphincter 10. Flange 52 around pumping reservoir 14 secures the pumping reservoir 14 in place, and engages tubing 60. Preferably, a surgeon anchors flange 52 by using suture sites 55. Tubing 60 connects the pumping reservoir 14 to the cuff portion 16. In operation, the pumping reservoir 14 controls the ingress and egress of fluid to and from the cuff portion 16. The ingress and egress of fluid radially contracts and expands, respectively, the cuff portion 16.

When deployed, the cuff portion 16 surrounds the internal anal sphincter at the level of the superior rectum below the descending sigmoid colon. The tubing 60 is routed toward the body wall and the pumping reservoir 14 is secured to the internal peritoneum of the lower abdomen 2. It is envisioned that the pumping reservoir 14 could be mounted to the body wall of the flank superior to the iliac crest to avoid invading the peritoneal space or to such other location as may be indicated by the patient's anatomy or the surgeon's preference.

I. The Artificial Sphincter

Figure 2:
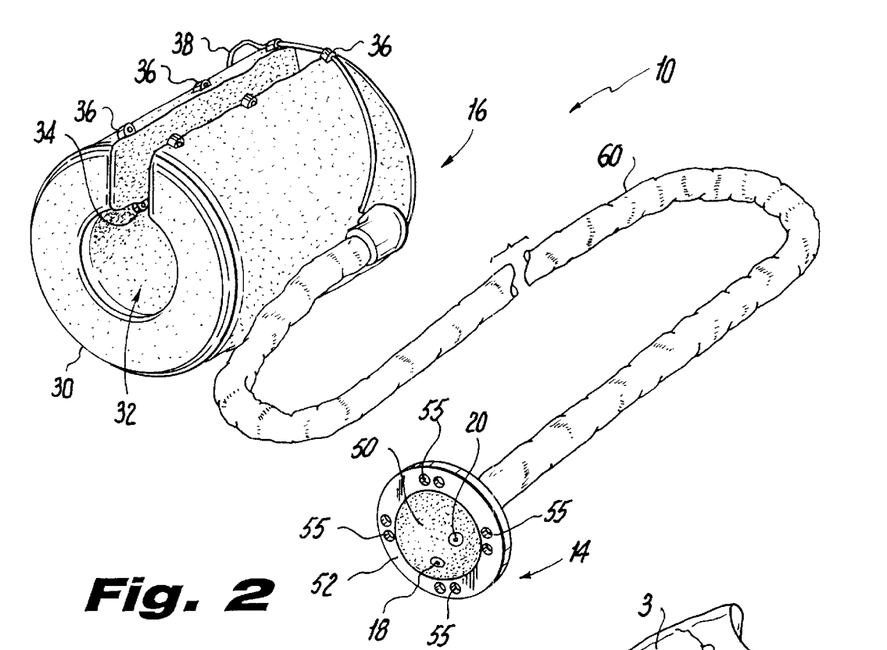
FIG. 2 is a perspective view of an artificial sphincter constructed in accordance with a preferred embodiment of the subject disclosure.
Figure 3:
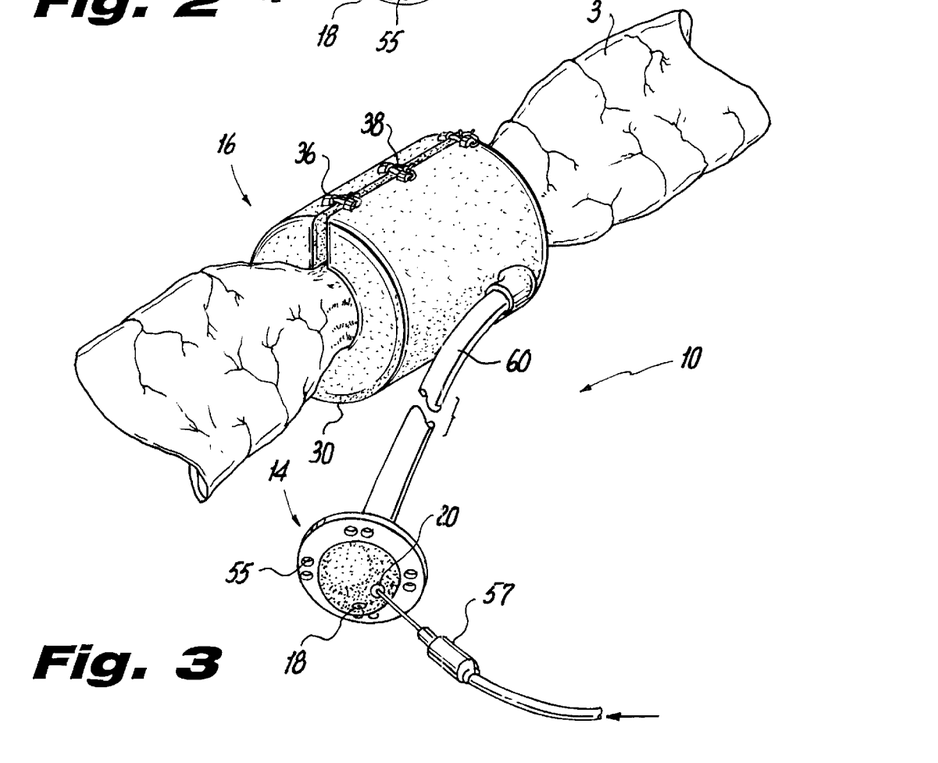
FIG. 3 is a perspective view of the artificial sphincter of FIG. 1 disposed in an operational position occluding a body conduit.

Referring to FIGS. 2 and 3, there are shown perspective views of an artificial sphincter 10 unassembled and assembled in an occluded condition on a body conduit 3, respectively. The cuff portion 16 has an elastic inner radial portion 32 and, as hydraulic pressure increases through the introduction of fluid, the elastic inner radial portion 32 radially contracts to occlude the patient's body conduit 3. It is envisioned that the cuff portion 16 may include a split sleeve as illustrated, a partial occlusion coil, or any shape as appropriate for the specific patient and application.

In another embodiment, the cuff portion 16 may include a plurality of arcuate portions which are selectively engaged to form a desired length. The plurality of arcuate portions serve to effectively spread the pressure required to occlude the bowel over a greater area thereby reducing risk of local tissue damage. Further, the selection of an appropriate length by the surgeon enhances performance of the subject device. It is envisioned that the connectors which couple the plurality of arcuate portions may be needleless connectors which support bi-directional flow (as are available from Becton Dickinson and Company, 1 Becton Drive, Franklin Lakes, N.J. USA 07417), ¼ turn Luer locks, snap fit friction couplings with o-rings or any suitable leak-proof fitting as is known to those skilled in the art.

To prevent migration of cuff portion 16, suture sites 34 are provided along the inner radius 32 of the cuff portion 16. Grommets 36 are provided along the outer radius 30. Multiple filaments 38 lace through the grommets 36 to allow fine tuning of the fit of the cuff portion 16. Preferably, a surgeon secures the cuff portion 16 to an individual's body conduit by the combination of lacing and suturing. However, it is also envisioned that the laces and the suture sites 34 separately are sufficient to secure the artificial sphincter 10 in a location as selected by a surgeon. It is envisioned that the length of the tubing 60 may be extended by connecting multiple tube sections with couplings to create the tubing 60. Such extending tube sections will accommodate various anatomical attachment positions.

Figure 4:
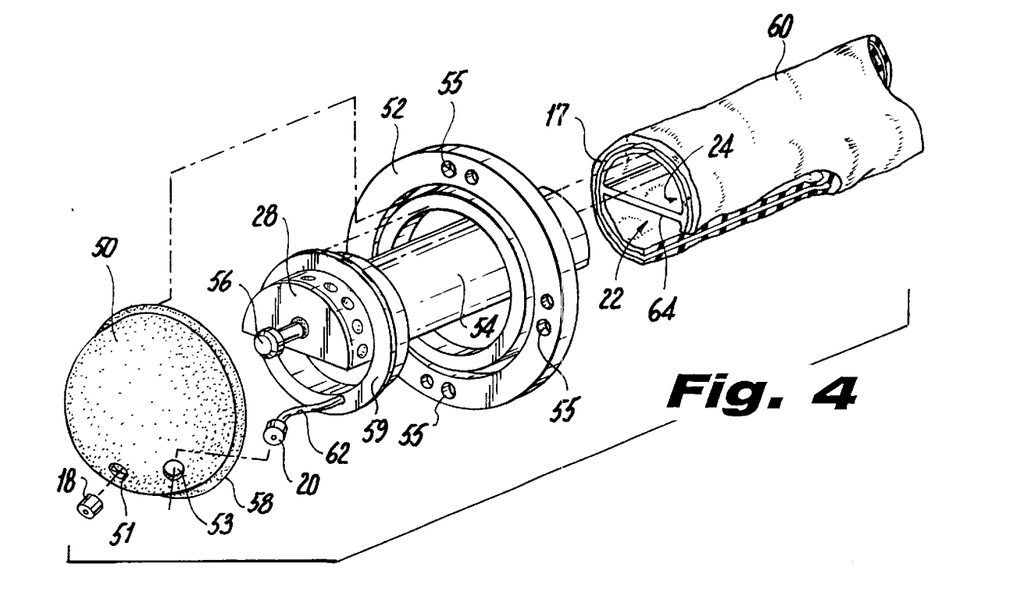
FIG. 4 is an exploded perspective view of an artificial sphincter constructed in accordance with the subject disclosure, the components including a pumping reservoir, a normally closed valve and tubing.

Referring to FIG. 4, tubing 60 defines an outlet passageway 24, an inlet passageway 22 and a portion of the inflatable lumen 17. The outlet passageway 24 partially houses a normally closed spring-loaded release valve 28. Pumping reservoir 14 houses the remaining portion of normally closed valve 28. Pumping reservoir 14 preferably includes a dome 50 of generally hemispheric configuration. The dome 50 defines a first aperture 51 and a second aperture 53 for sealingly receiving the first injection port 18 and the second injection port 20, respectively. An annular rim 58 provides structural support to the dome 50. The flange 52 couples to the annular rim 58 of the dome 50. Suture sites 55 are provided in the flange 52 to enable a surgeon to secure the pumping reservoir 14 in a sub-dermal location.

Normally closed valve 28 has a valve housing 54 in the form of a fenestrated baffle conduit. A plunger 56 extends axially from a proximal end of the normally closed valve 28 into the dome 50. A shoulder 59 mounts normally closed valve 28 to the flange 52. Further, the shoulder 59 defines a bore for receiving a fluid conducting lead 62 from the second injection port 20. The fluid conducting lead 62 is in fluid communication with inflatable lumen 17. The tubing 60 is divided into the inlet passageway 22 and the outlet passageway 24 by an internal wall 64. The distal end of the normally closed valve 28 extends into the outlet passageway 24.

Figure 5:
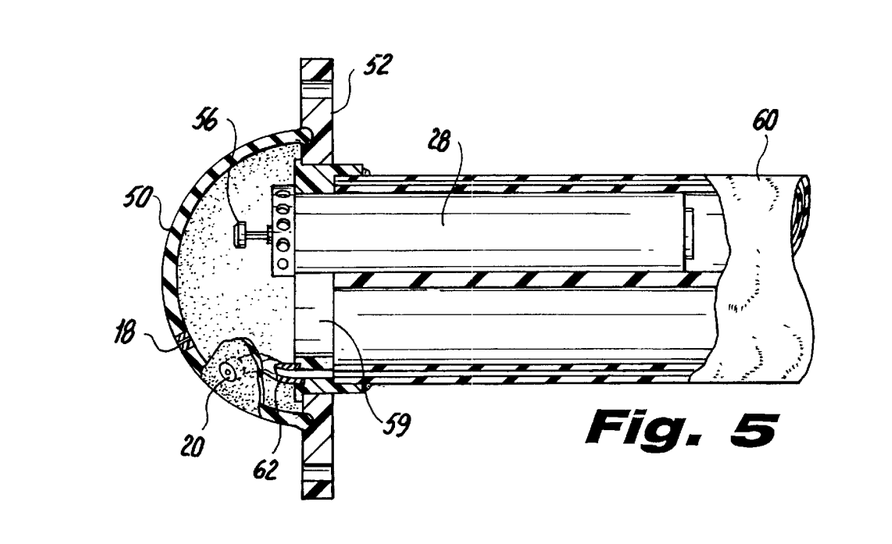
FIG. 5 is an assembled cross-sectional view of the pumping reservoir, normally closed valve and tubing of FIG. 4.

Now referring to FIG. 5, shoulder 59 locks the normally closed valve 28 in relation to the flange 52. Further, shoulder 59 receives tubing 60 in a fluid tight seal. Preferably, plunger 56 and a portion of the proximal end of valve 28 extend partially into the dome 50. The valve housing 54 extends into the outlet passageway 24 such that fluid cannot pass through the outlet passageway 24 without passing through valve 28. The distal end of valve 28 terminates within outlet passageway 24. The first injection port 18 is in fluid communication with the inlet passageway 22 and the second injection port 20 is in fluid communication with the inflatable lumen 17.

Figure 6:
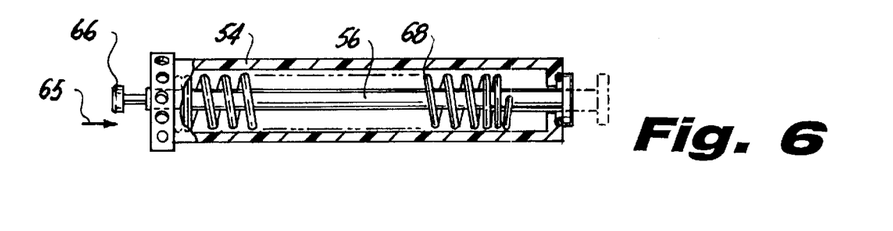
FIG. 6 is a cross-sectional view of a normally closed spring-loaded release valve of FIG. 4 in a closed position and in an open position in phantom lines.

Referring to FIG. 6, the plunger 56 is located within the valve housing 54 and is biased in a closed position by a spring 68. The proximal end of the plunger 56 has a head 66 to enable location and manual depression of the plunger 56 within the pumping reservoir 14. In another embodiment, the proximal end of the plunger 56 is bulbous in shape. The distal end of the plunger 56 has a "T" shaped configuration to normally prevent flow through the opening of the valve housing 54. Thus, when the valve 28 is closed, fluid cannot pass through the outlet passageway 24. Depression in the direction indicated by arrow 65 of the head 66 enables overcoming the force of spring 58 to displace the T-shaped distal end as shown in phantom line. As a result of the plunger 56 being displaced, fluid can pass through the outlet passageway 24 from the cuff portion 16 into pumping reservoir 14.

Figure 7:
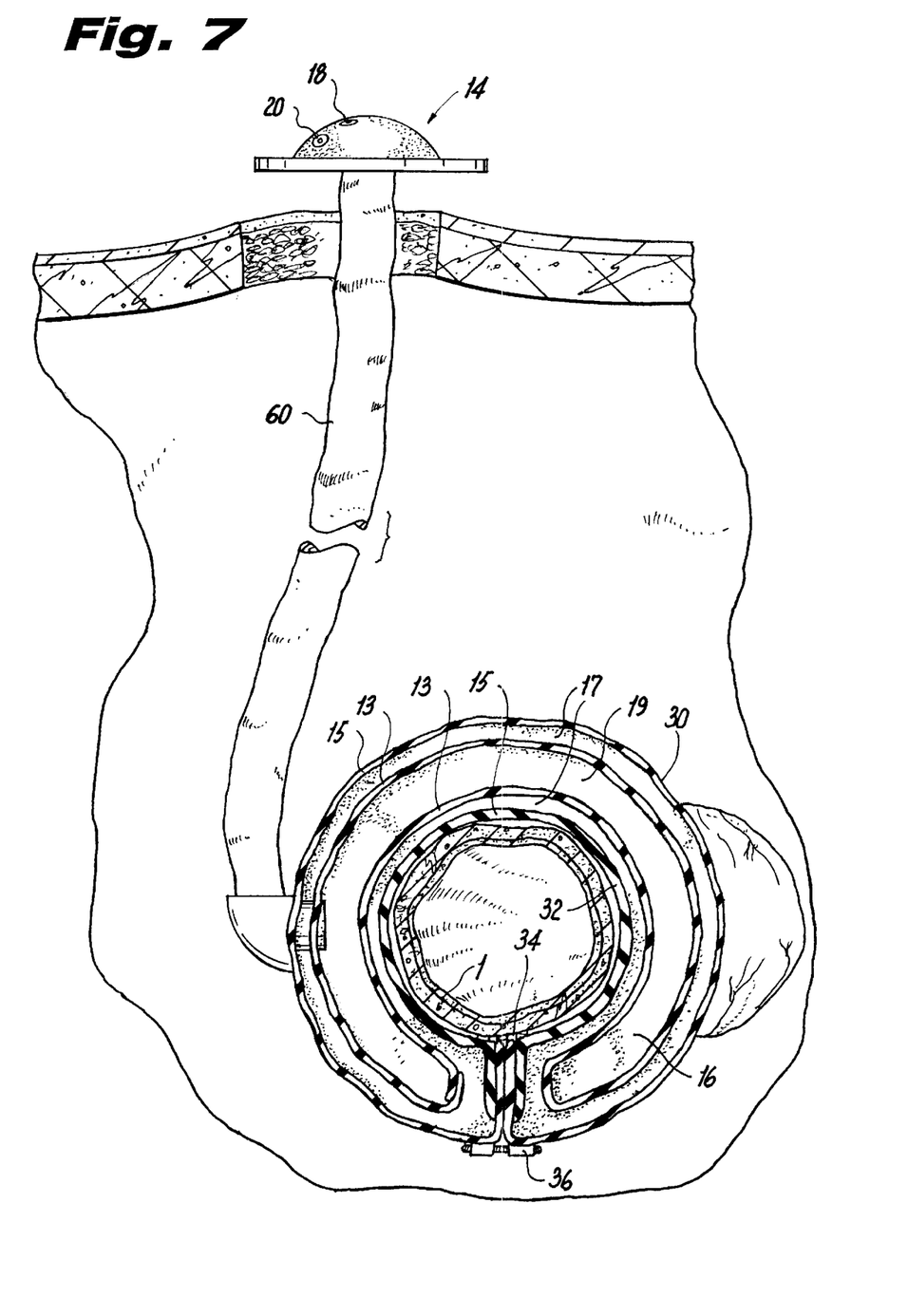
FIG. 7 is a partial cross-sectional view of an artificial sphincter constructed in accordance with the subject disclosure in a deflated state during surgical implantation.

Referring to FIG. 7, the outer radius 30 of cuff portion 16 is defined by an exterior wall portion 15 and an interior wall portion 13. An inflatable lumen 17 is defined between the exterior wall portion 15 and the interior wall portion 13 for providing structural rigidity to the artificial sphincter 10 during use. Inflatable lumen 17 preferably extends throughout the circumference of artificial sphincter 10. Therefore, a surgeon can control the hydraulic pressure within the inflatable lumen 17 to provide the desired rigidity and hydraulic balance between the cuff portion 16 and the pumping reservoir 14. Proper inflation of the inflatable lumen 17 protects the underlying tissue from damage which can be caused by an overly rigid or improperly balanced system. The even distribution of pressure by inflatable lumen 17 is of particular importance where delicate tissue is concerned.

Interior wall portion 13 and exterior wall portion 15 each contain an elastic inner radial portion 32. The interior wall portion 13 of cuff portion 16 forms a lumen 19 for occluding a body passageway. Preferably, occluding lumen 19 extends throughout the tubing 60 and into the pumping reservoir 14 such that the occluding lumen 19 is in fluid communication with the pumping reservoir 14. The second injection port 20 of pumping reservoir 14 allows a surgeon to insert hydraulic fluid into the pumping reservoir 14. The injection ports 18 and 20 may be selected from many types known to those skilled in the art such as needle valves as shown or sealed Luer lock-injection ports. The hydraulic fluid may be selected from a variety of well known biocompatible sterile fluids, such as saline, sterile water and the like.

II. Surgical Implantation of the Artificial Sphincter

Still referring to FIG. 7, to secure the cuff portion 16 in place a surgeon sutures the cuff portion 16 to the bowel or the annular ring musculature of the distal bowel. The inflatable lumen 17 and the occluding lumen 19 are deflated. Thus, the cuff portion 16, the tubing 60 and the pumping reservoir 14 are in a non-rigid contracted state.

Figure 8:
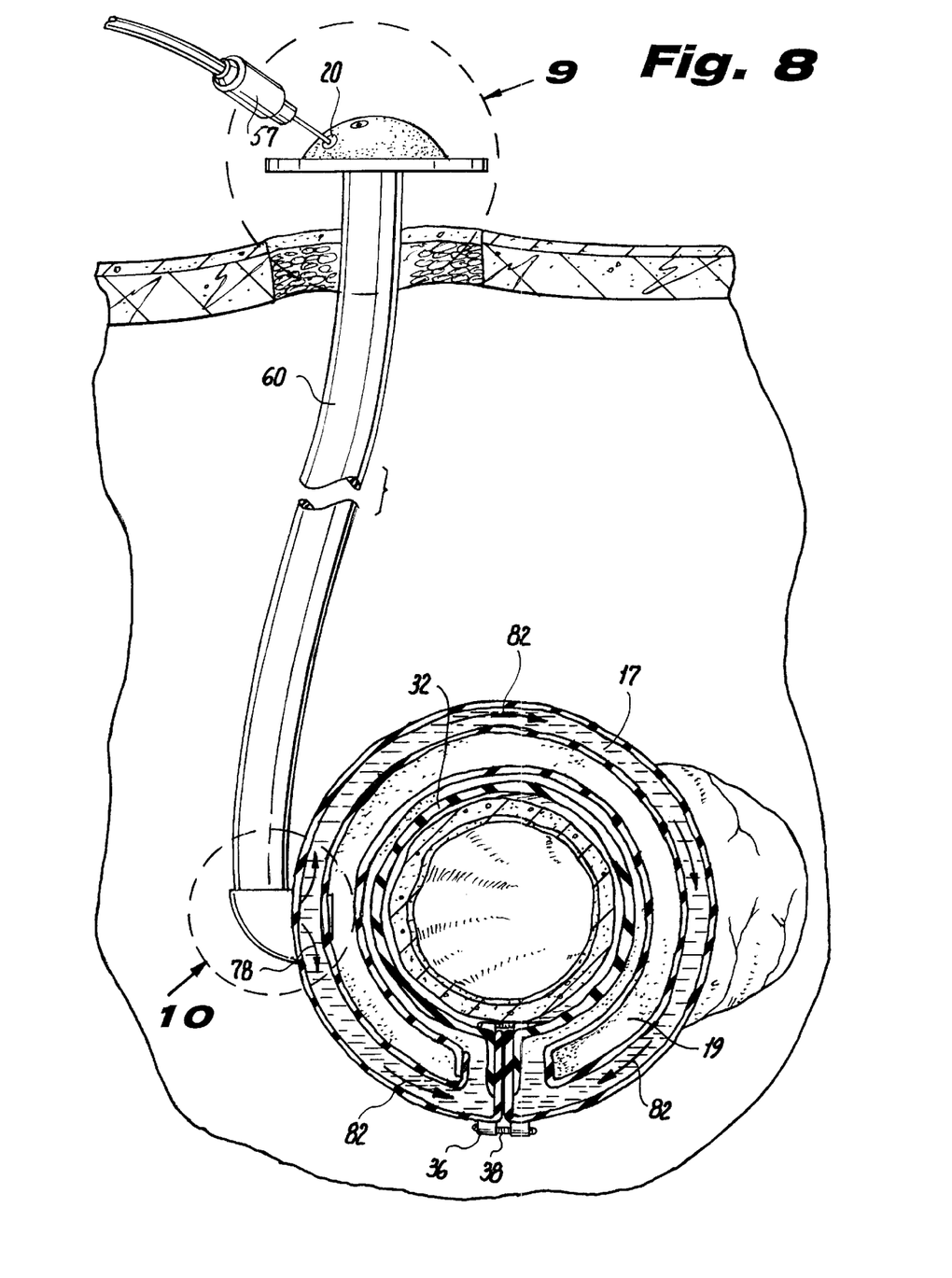
FIG. 8 is a partial cross-sectional view of the artificial sphincter of FIG. 7 illustrated with a first injection port being used to fill the outer lumen of the device during surgical implantation of the artificial sphincter.
Figure 9:
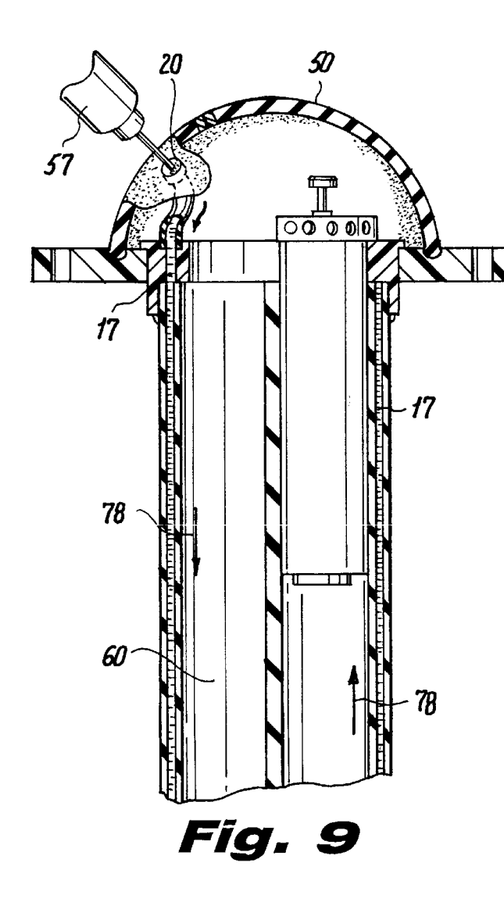
FIG. 9 is an enlarged localized cross-sectional view of the upper portion of the pumping reservoir as shown in FIG. 8.
Figure 10:
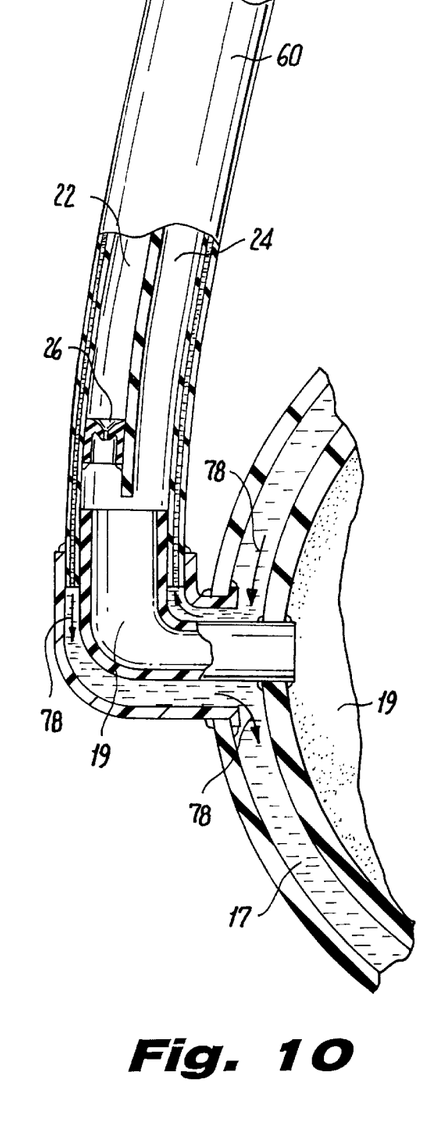
FIG. 10 is another enlarged localized cross-sectional view of the tubing connection to the cuff portion as shown in FIG. 8.

Referring now to FIGS. 8, 9 and 10, after suturing the cuff portion 16 in place, a surgeon uses a syringe device 57 to pierce the second injection port 20 to inject fluid into the inflatable lumen 17. The fluid will flow generally in the direction indicated by arrows 78 until the inflatable lumen 17 is inflated. As the pressure within the inflatable lumen 17 increases, the pumping reservoir 14, the tubing 60 and the cuff portion 16 gain structural integrity. Using the syringe device 57, the surgeon can inflate and deflate the inflatable lumen 17 until the pumping reservoir 14, the tubing 60 and the cuff portion 16 have the desired rigidity. In another embodiment, the inflatable lumen 17 extends substantially throughout the dome 50 of the pumping reservoir 14.

The inlet passageway 22 and the outlet passageway 24 comprise tubing 60. The inlet passageway 22 has a one-way check valve 26 disposed within occluding lumen 19 to allow fluid to pass only from the pumping reservoir 14 into the cuff portion 16. Tubing 60 also allows fluid to flow within inflatable lumen 17 as indicated by arrows 78.

The surgeon insures that the inflatable lumen 17 is sufficiently cushioned to mitigate any potential tissue damage. Further, the surgeon insures that the fluid balance between the cuff portion 16 and the pumping reservoir 14 is optimized. As required in the judgement of the surgeon, fluid is added through the second injection port 20 to the inflatable lumen 17 in the direction indicated by arrows 78 using a syringe device 57. When filled properly with fluid, the inflatable lumen 17 provides cushion to prevent unnecessary tissue damage.

Figure 11:
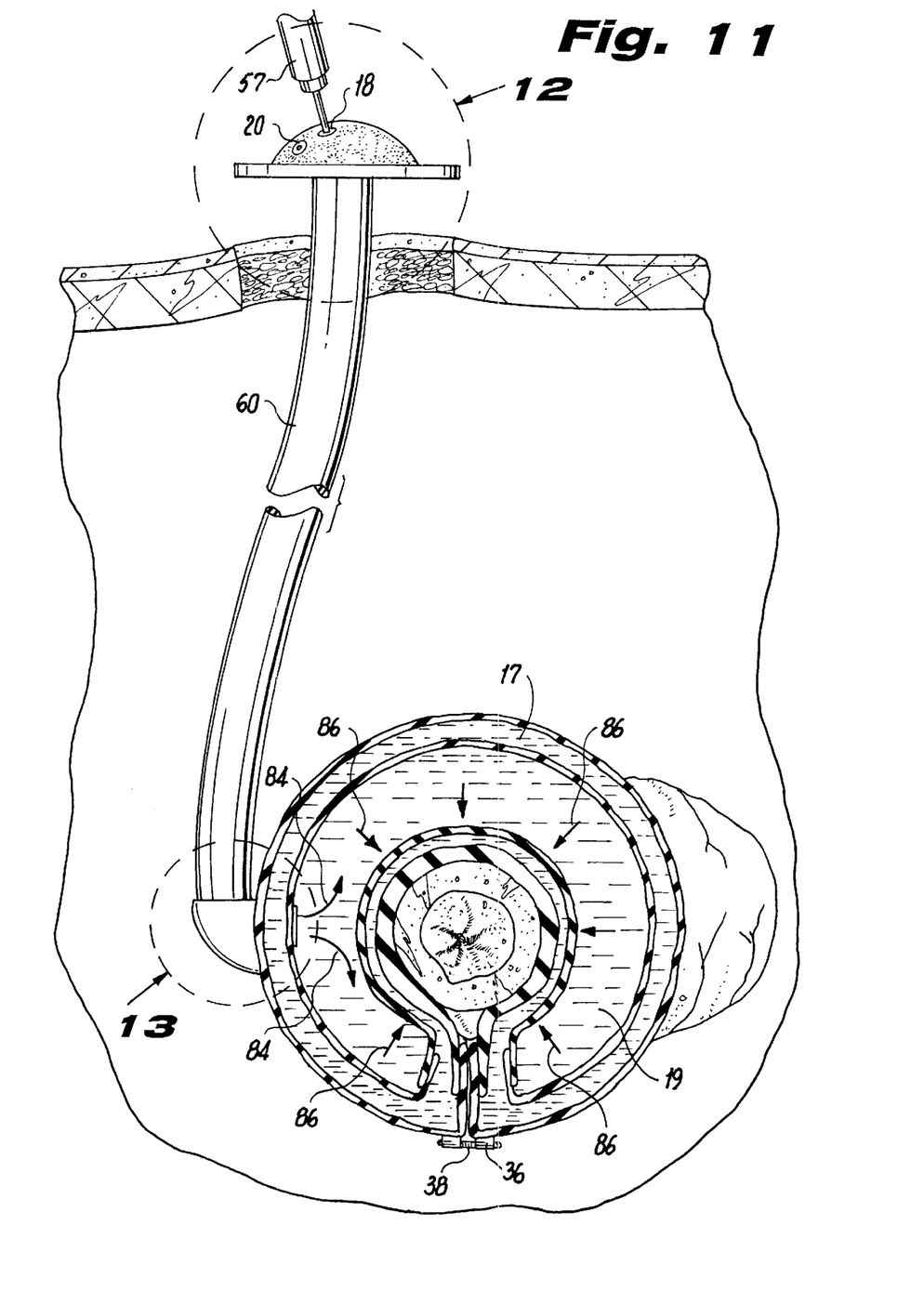
FIG. 11 is a partial cross-sectional view of the artificial sphincter of FIG. 7 illustrated with a second injection port being used to fill the inner lumen of the device during surgical implantation of the artificial sphincter.
Figure 12:
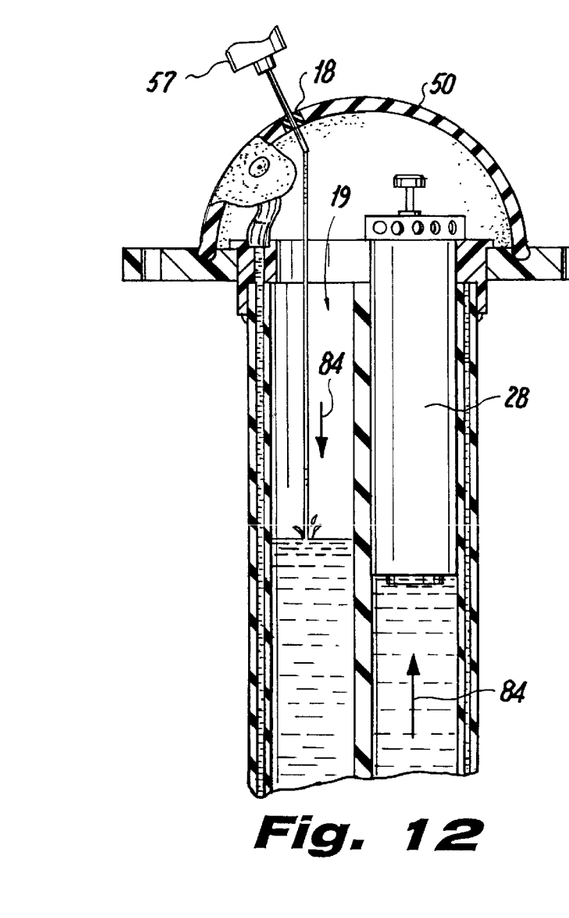
FIG. 12 is an enlarged localized cross-sectional view of the upper portion of the pumping reservoir as shown in FIG. 11.
Figure 13:
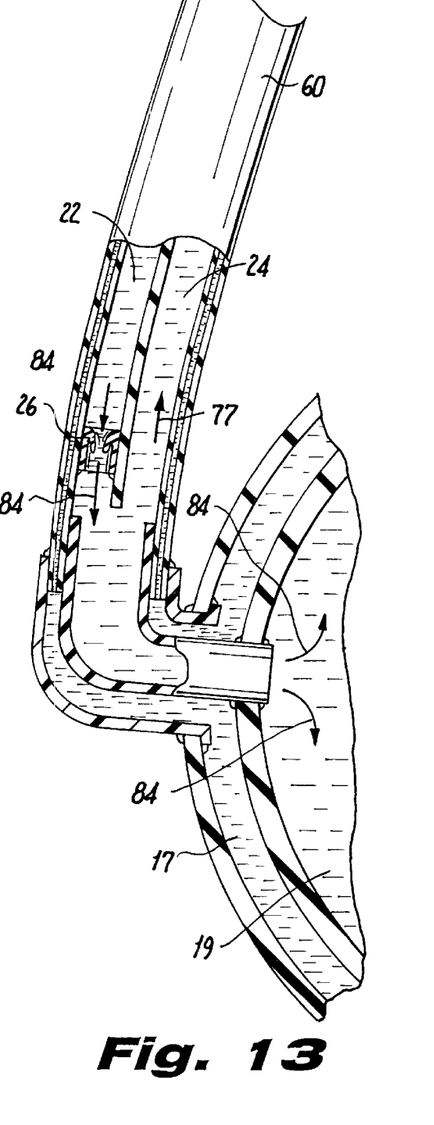
FIG. 13 is another enlarged localized cross-sectional view of the tubing connection to the cuff portion as shown in FIG. 11.

Now referring to FIGS. 11, 12 and 13, prior to completing the surgical implantation procedure, the surgeon adds fluid to the occluding lumen 19 in the direction indicated by arrows 84 using a syringe device 57. The normally closed valve 28 disposed within the outlet passageway 24 and one-way check valve 26 disposed within the inlet passageway 22 prevent flow out of the cuff portion 16. Thus, once the surgeon increases pressure with the cuff portion 16, it is maintained therein even though the pumping reservoir is at a lower pressure. Upon completion of radial contraction of the elastic inner radial portion 32 of the cuff portion 16 in the direction indicated by arrows 86, the bowel is occluded with a minimal potential for tissue damage. Further, the patient will be ambulatory without fear of unwanted bowel evacuation and undue discomfort. To complete the surgical implementation, the surgeon sutures the pumping reservoir 14 in a suitable location beneath the skin of the patient.

In another embodiment, a single tube may be in fluid communication between pumping reservoir 14 and cuff portion 16. Preferably, the single tube contains a non-return valve which can be manually deformed to allow cuff portion 16 to drain into pumping reservoir 14. In another embodiment, the occluding lumen 19 and the inflatable lumen 17 can be inflated with a gas such as air. In still another embodiment, the first injection port 18 and second injection port 20 are ¼ turn female Luer locks to allow a surgeon to reversibly inflate the occluding lumen 19 and the inflatable lumen 17.

III. Utilization by a Patient

Figure 14:
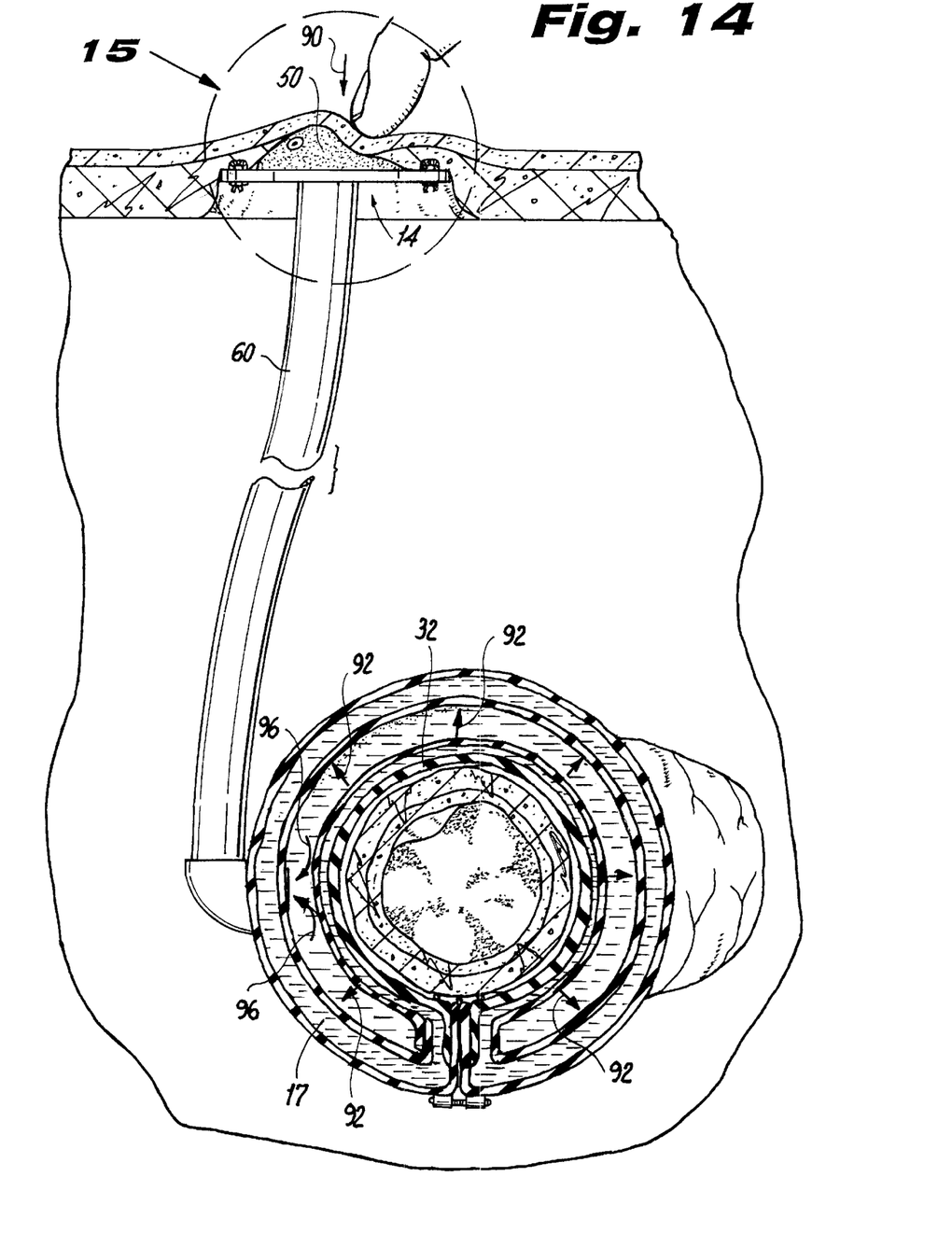
FIG. 14 is a partial cross-sectional view of an artificial sphincter constructed in accordance with the subject disclosure fully disposed in an operational position on a patient who is actuating the normally closed valve to evacuate the bowel.
Figure 15:
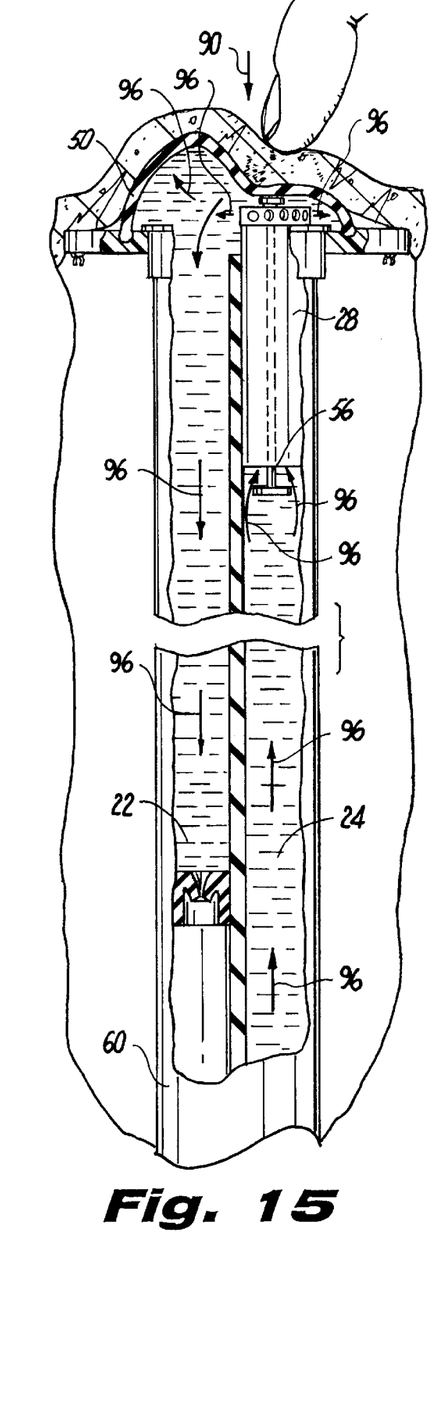
FIG. 15 is a localized cross-sectional view of FIG. 14 with the normally closed valve in the open position.

Referring to FIGS. 14 and 15, when a patient desires to evacuate their bowel, the patient manually actuates the normally closed valve 28. The patient needs to locate the pumping reservoir 14. As noted above, the plunger 56 is located within the dome 50 of pumping reservoir 14. The plunger 56 of the valve 28 is depressed in the direction indicated by arrow 90 to open the normally closed valve 28. When the normally closed valve 28 is in the open position, fluid flows in the direction as indicated by arrows 96 from the higher pressure cuff portion 16 into the relatively lower pressure area within the pumping reservoir 14 and the normally closed valve 28. The fluid flow out of the cuff portion 16 reduces the hydraulic pressure within the cuff portion 16. As a result, the elastic inner radial portion 32 contracts in the direction indicated by arrows 92 and the cuff portion 16 relaxes the rectal constriction to allow the bowel to evacuate. At such time the patient can release the plunger 56 and the valve 28 springs closed.

Figure 16:
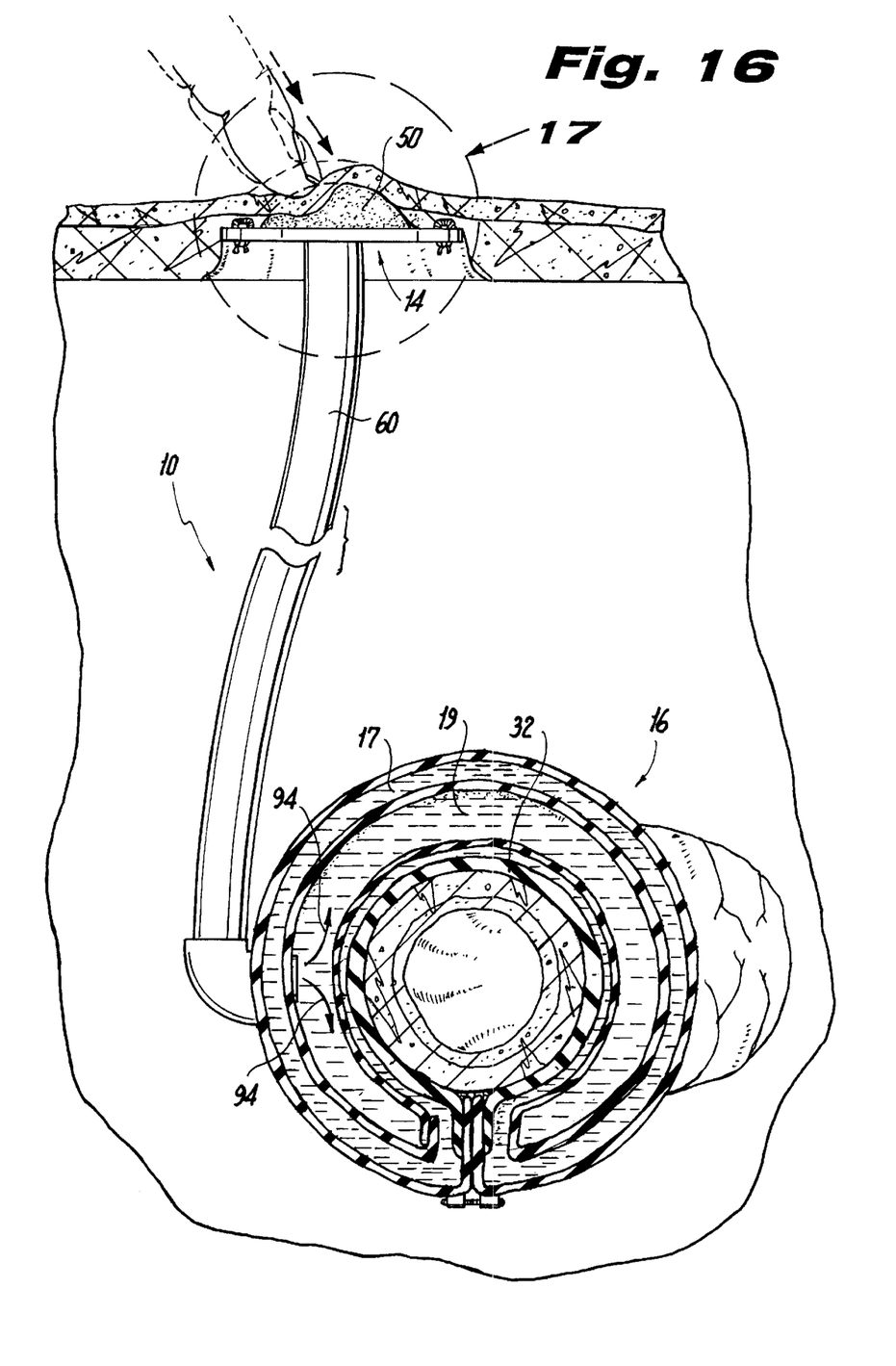
FIG. 16 a partial cross-sectional view of an artificial sphincter constructed in accordance with the subject disclosure fully disposed in an operational position on a patient who is actuating the pumping reservoir to occlude the bowel.
Figure 17:
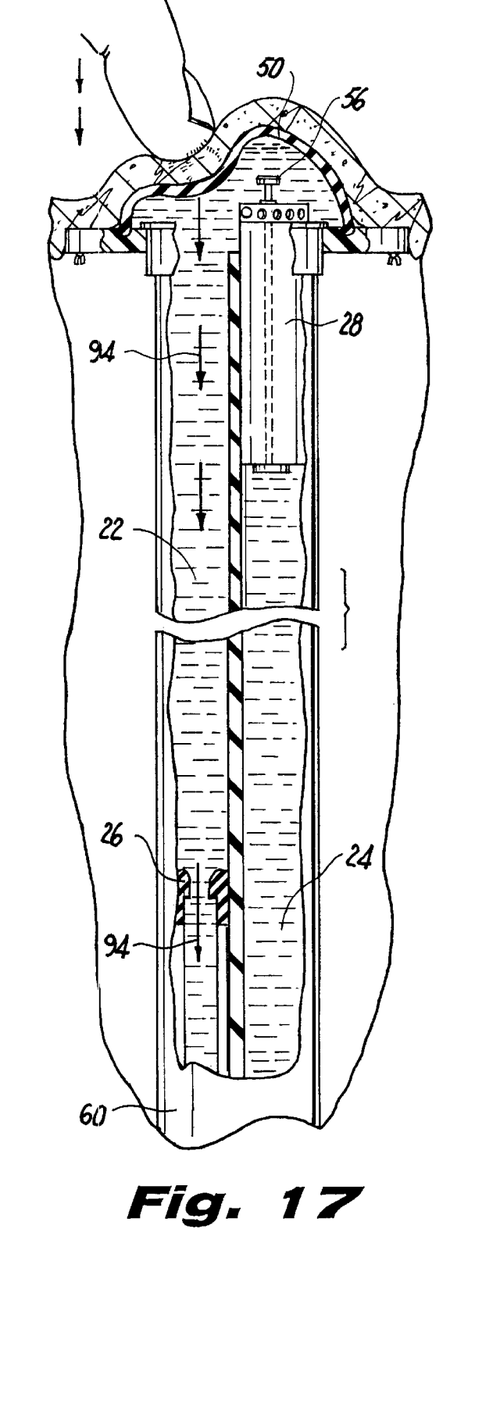
FIG. 17 is a localized cross-sectional view of the pumping reservoir as shown in FIG. 16 with the pumping reservoir being manually actuated to occlude the bowel.

Referring to FIGS. 16 and 17, after evacuation of the bowel, the patient manually initiates occlusion of the bowel. To actuate the artificial sphincter 10 to occlude the bowel, the patient depresses the sub-dermal pumping reservoir 14 while coincidentally avoiding depression of the plunger 56. Depression of the dome 50 increases the hydraulic pressure within the inlet passageway 22 until the bias of the one-way check valve 26 is overcome. When the bias force of the check valve 26 is overcome, fluid passes in the direction indicated by arrows 94 through the one-way check valve 26 to increase hydraulic pressure within the cuff portion 16. The normally closed valve 28 prevents fluid flow through the outlet passageway 24 and maintains pressure within the occluding lumen 19 of the cuff portion 16. As a result of the increased pressure within the cuff portion 16, the inner elastic radial portion 32 of the cuff 16 expands as described above with reference to FIG. 13. The expansion of the inner elastic radial portion 32 restricts the bowel at the level of the superior rectum. Thus, cuff portion 16 serves the function of the internal anal sphincter muscle. Once evacuation of the bowel is desired again, the individual again depresses the plunger 56 of the valve 28 within the pumping reservoir 14 as described with respect to FIGS. 14 and 15.

In another embodiment, the inflatable lumen 17 does not extend throughout the artificial sphincter 10, but only extends over a section of the cuff portion 16. Notwithstanding the operative reliability of the preferred embodiments, it is envisioned that a radio-opaque dye within the fluid may be utilized. In the rare event that problems later develop, the dye enables investigation with conventional X-ray techniques. In another embodiment, the cuff portion 16 is implanted to press against the corpus spongiosum so as to constrict the urethra when expanded to act as a urinary incontinence device. The pumping reservoir 14 can be mounted in the patient's dartos pouch or other suitable location as decided by the surgeon.

While the subject invention has been described with respect to preferred embodiments, it will be appreciated by those skilled in the art that the principles and inventive concepts could be applied in various application obvious to those skilled in the art of occluding real and artificial body passageways. Further, those skilled in the art will readily appreciate that various changes and/or modifications can be made thereto without departing from the spirit or scope as defined by the appended claims.

What is claimed is:

1. An implantable device for controlling the flow of matter through a body conduit of a patient, comprising:
   a) a wall portion defining or including lumen configured to substantially encircle a section of a body conduit;
   b) an inlet conduit operatively connected to the cuff portion for delivering fluid thereto, the inlet conduit having a first flow control device operatively associated therewith;
   c) an outlet conduit operatively connected to the cuff portion for releasing fluid therefrom, the outlet conduit having a second flow control device operatively associated therewith;
   d) a pumping reservoir in fluid communication with the inlet conduit and the outlet conduit, wherein actuation of the pumping reservoir causes fluid to ingress into the cuff portion such that the cuff portion radially contracts and actuation of the second flow control device causes fluid to egress from the cuff portion such that the cuff portion radially expands; and
   e) a second lumen surrounding said wall portion for admitting a fluid to provide rigidity and balance pressure between said wall portion and the pumping reservoir.

2. A device as recited in claim 1, further comprising a first injection port for injecting fluid into the second lumen and a second injection port for injecting fluid into the pumping reservoir.

3. A device as recited in claim 1, wherein the second flow control device is a normal closed valve at least partially disposed within the pumping reservoir.

4. A device as recited in claim 1, wherein said wall portion includes a plurality of continuous coils adapted to occlude the section of the body conduit.

5. A device as recited in claim 1, wherein the first flow control device is opened by a high pressure condition in the pumping reservoir and the second flow control device is selectively opened by the patient.

6. A device as recited in claim 1, wherein the second lumen surrounds the pumping reservoir, the inlet conduit and the outlet conduit.

7. A device as recited in claim 1, further comprising grommets disposed on an outer circumference of wall portion to secure the wall portion about the section of the body conduit.

8. A device as recited in claim 1, wherein the wall portion has inner and outer circumferential surfaces and the second lumen surrounds the inner and outer circumferential surfaces.

9. An implantable device for reversibly closing a body passage comprising:
  (a) at least one coil including: (i) a flexible inner housing defining a first lumen, the flexible inner housing adapted for movement between an inflated condition wherein the body passageway is blocked and a deflated condition wherein the body passageway is unblocked; and (ii) an outer portion for providing structural support to the at least one coil and defining a second lumen;
  (b) a port to inject fluid into the second lumen for adjusting regidity of the coil;
  (c) a reservoir for storing fluid to inflate and deflate the first lumen of the at least one coil; and
  (d) at least one tube, connecting the at least one coil to the reservoir, having at least one valve to prevent backflow of fluid from the at least one coil into the reservoir and to allow fluid to flow from the at least one coil into the reservoir.

10. A device as recited in claim 9, wherein the outer portion surrounds the at least one tube and the reservoir.

11. A device as recited in claim 9, wherein the at least one valve is a one way check valve in an inlet tube and a normally closed valve in an outlet tube.

12. A device as recited in claim 9, wherein the at least one tube includes a connector for coupling an additional length of tube.

13. A device as recited in claim 9, further comprising a second port to inject fluid into the reservoir for communication to and from the at lest one coil.

14. A device as recited in claim 12, wherein the fluid in the second lumen and the fluid in the reservoir are selected from the group consisting of saline, saline with a dye, sterile water and sterile water with a dye.

15. An artificial sphincter for controlling incontinence comprising:
  a cuff portion having an outer wall, an intermediate wall and a flexible inner wall, said outer wall and said intermediate wall defining a first lumen therebetween, said intermediate wall and said flexible inner wall defining a second lumen therebetween;
  a pumping reservoir configured to conduct fluid for reversibly inflating said second lumen; and
  at least one fluid conducting path in communication with the cuff and the pumping reservoir.

16. An artificial sphincter as recited in claim 15, further comprising a first injection port to inject a biocompatible fluid into the first lumen for adjusting rigidity of the cuff portion.

17. A device as recited in claim 16, further comprising a second port to inject a biocompatible fluid into the second lumen.

18. An artificial sphincter, comprising:
  a) an inflatable cuff for occluding a body passageway, said inflatable cuff having an interior wall portion and an exterior wall portion, a first lumen defined between the exterior wall portion and the interior wall portion, and a second lumen defined by the interior wall portion; and
  b) a pumping reservoir in fluid communication with the inflatable cuff for controlling the ingress and egress of fluid to and from the second lumen to cause the inflatable cuff to radially contract and expand relative to the body passageway.

19. An artificial sphincter as recited in claim 18, further comprising suture sites on an inner circumference of the inflatable cuff to anchor the inflatable in a position.

20. An artificial sphincter as recited in claim 18, further comprising grommets disposed on an outer circumference of the inflatable cuff for adjusting a fit of the inflatable cuff and for securing the inflatable in a position.

* * * * *

UNITED STATES PATENT AND TRADEMARK OFFICE
CERTIFICATE OF CORRECTION

PATENT NO.     : 6,491,623 B2
DATED          : December 10, 2002
INVENTOR(S)    : Daniel R. and Harriet A. Fellows It is certified that error appears in the above-identified patent and that said Letters Patent is hereby corrected as shown below:

Column 8,
Line 43, please delete the words "or including" and insert in their place
-- an occluding --;
Lines 45, 49, 56 (twice), and 58 (twice) please delete the word "cuff" and insert in its place -- wall --;

Column 10,
Line 3, please delete the word "lest" and insert in its place -- least --.

Signed and Sealed this

Twenty-second Day of April, 2003

JAMES E. ROGAN
*Director of the United States Patent and Trademark Office*